(12) United States Patent
Greeley et al.

(10) Patent No.: US 12,402,933 B2
(45) Date of Patent: Sep. 2, 2025

(54) ILLUMINATED ELECTROSURGICAL DEVICES, SYSTEMS AND METHODS

(71) Applicant: Medtronic Advanced Energy LLC, Minneapolis, MN (US)

(72) Inventors: Roger Greeley, Portsmouth, NH (US); David Hubelbank, Portsmouth, NH (US); Ethan Carter, Epping, NH (US); Xiaoming Cheng, Keller, TX (US); William Siopes, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1261 days.

(21) Appl. No.: 16/264,075

(22) Filed: Jan. 31, 2019

(65) Prior Publication Data
US 2019/0321093 A1 Oct. 24, 2019

Related U.S. Application Data

(60) Provisional application No. 62/660,396, filed on Apr. 20, 2018.

(51) Int. Cl.
*A61B 18/14* (2006.01)
*A61B 18/12* (2006.01)
(Continued)

(52) U.S. Cl.
CPC ...... *A61B 18/1442* (2013.01); *A61B 18/1206* (2013.01); *A61B 90/30* (2016.02);
(Continued)

(58) Field of Classification Search
CPC .. A61B 2018/00107; A61B 2018/1412; A61B 1/06; A61B 90/30; A61B 2090/306; A61B 2090/309
See application file for complete search history.

(56) References Cited

U.S. PATENT DOCUMENTS

| 7,731,388 B2 | 6/2010 | Hoelen et al. |
| 7,736,361 B2 | 6/2010 | Palanker et al. |

(Continued)

FOREIGN PATENT DOCUMENTS

| WO | WO-2006043195 A1 * | 4/2006 | ............. F21V 13/04 |
| WO | WO 2017/176240 | 10/2017 | |

OTHER PUBLICATIONS

International Search Report and Written Opinion from PCT Application PCT/US2019/016065, dated May 3, 2019, 12 pgs.
(Continued)

*Primary Examiner* — Linda C Dvorak
*Assistant Examiner* — Christine A Dedoulis
(74) *Attorney, Agent, or Firm* — Husch Blackwell LLP

(57) ABSTRACT

Embodiments relate to illuminated electrosurgical devices and related systems and methods. An electrosurgical device can include an electrosurgical blade having a proximal end and a distal end and comprising a dielectric coating, at least one of the electrosurgical blade or the dielectric coating including at least one light-guiding element, an optic having a proximal end and a distal end, the distal end of the optic optically coupled to the proximal end of the electrosurgical blade, and a light source arranged at the proximal end of the optic and configured to provide light that is guided through the optic and the at least one light-guiding element to illuminate an area around the distal end of the electrosurgical blade.

25 Claims, 14 Drawing Sheets

(51) Int. Cl.
   *A61B 90/30*     (2016.01)
   *A61B 18/00*     (2006.01)
(52) U.S. Cl.
   CPC ............... *A61B 2018/00589* (2013.01); *A61B 2018/00601* (2013.01); *A61B 2018/1412* (2013.01)

(56) References Cited

U.S. PATENT DOCUMENTS

| | | | |
|---|---|---|---|
| 10,463,444 B2* | 11/2019 | Davis ................. | A61B 17/3211 |
| 2014/0005555 A1* | 1/2014 | Tesar ................. | A61B 17/0218 |
| | | | 600/476 |
| 2014/0277296 A1 | 9/2014 | Tolosa et al. | |
| 2016/0015467 A1 | 1/2016 | Vayser et al. | |
| 2016/0120592 A1 | 5/2016 | Sylvester et al. | |
| 2016/0157920 A1* | 6/2016 | Vayser ................. | A61B 90/30 |
| | | | 600/249 |
| 2017/0172646 A1 | 6/2017 | Patel et al. | |
| 2019/0380805 A1 | 12/2019 | Greeley et al. | |

OTHER PUBLICATIONS

International Preliminary Report on Patentability from PCT Application PCT/US2019/016065, dated Oct. 29, 2020, 6 pgs.

* cited by examiner

ILLUMINATED ELECTROSURGICAL DEVICES, SYSTEMS AND METHODS

RELATED APPLICATION

This application claims the benefit of U.S. Provisional Application No. 62/660,396 filed on Apr. 20, 2018, the entirety of which is incorporated herein by reference.

TECHNICAL FIELD

This disclosure relates generally to electrosurgical devices and more particularly to electrosurgical devices with integrated illumination systems.

BACKGROUND

Electrosurgical devices generally include a handpiece (handle) ergonomically adapted for ease of manipulation by a surgeon during surgery, and for positioning an energy tip of the device to deliver electrical energy to a target tissue for tissue cutting or coagulation. An electrode and electrical supply cable are generally disposed within the handpiece, traversing from the handpiece's proximal end through the handpiece body, and terminating in an energy discharge tip at the distal end of the device. The electrical supply cable typically is connected to an energy source, such as a radiofrequency (RF) energy generator.

The handpiece or other portion of the device may include an illumination element for illuminating the surgical field. Light may be conducted towards the energy discharge tip and directed onto the surgical field via an optical waveguide coupled to the handpiece or disposed within the handpiece. The electrode may be disposed within the optical waveguide, or disposed alongside the waveguide. The electrode and waveguide may be disposed within a suitable supporting structure (for example, a cylindrical metal tube), that may be slidably extendable or retractable to permit the electrosurgical device to elongate or shorten as needed to treat the surgical site.

SUMMARY

Embodiments relate to illuminated electrosurgical devices and related systems and methods.

In one embodiment, an electrosurgical device comprises an electrosurgical blade having a proximal end and a distal end and comprising a dielectric coating, at least one of the electrosurgical blade or the dielectric coating including at least one light-guiding element, an optic having a proximal end and a distal end, the distal end of the optic optically coupled to the proximal end of the electrosurgical blade, and a light source arranged at the proximal end of the optic and configured to provide light that is guided through the optic and the at least one light-guiding element to illuminate an area around the distal end of the electrosurgical blade.

In another embodiment, a method comprises coating an electrosurgical blade having a proximal end and a distal end with a dielectric layer, forming at least one light-guiding element on at least one of the electrosurgical blade or the dielectric layer, optically coupling a distal end of an optic to the proximal end of the electrosurgical blade, and arranging a light source at a proximal end of the optic to provide light that is guided through the optic and the at least one light-guiding element of the dielectric layer to illuminate an area around the distal end of the electrosurgical blade.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
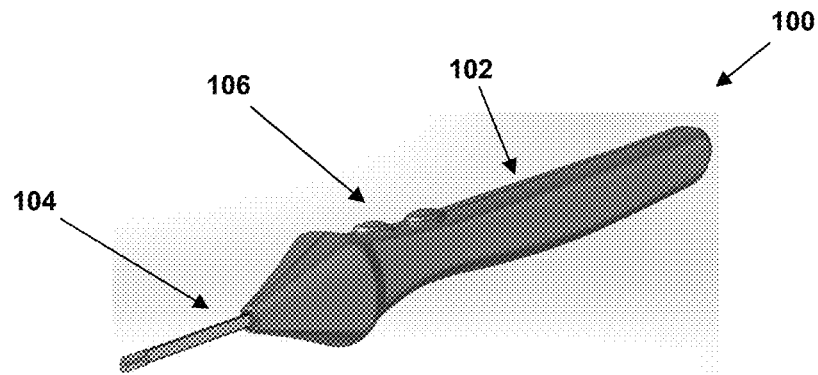
FIG. 1 depicts an electrosurgical device according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Unless the context indicates otherwise, the following terms shall have the following meaning and shall be applicable both to the singular and plural:

The term "electrosurgical device" means an electrical device designed for handheld use by a surgeon to dispense RF or other energy through the tip of an electrode into target surgical tissue, in order to cut or coagulate the tissue during a surgical procedure.

The terms "insulator," "insulation" and "insulating" mean electrically insulating, and refer to dielectric materials that permit little, if any, flow of electrical current through such material. Insulating materials may in some instances be thermal insulators but are not always so. Materials such as glass, metal oxides, porcelain, paper, plastics, polymers and rubbers are representative insulating materials.

The terms "radiofrequency energy" or "RF energy" mean energy from the electromagnetic spectrum having a frequency between about 3 kilohertz (3 kHz) and about 300 gigahertz (300 GHz).

The term "proximal" or "proximate," in the context of an area or end of a device or element means the operator end of the device or element, while the term "distal" means the patient end of the device or element.

Surgical devices should not unduly impede the surgeon's view of the operating field. This can be particularly troublesome in electrosurgical devices, especially those with extra features beyond energy delivery, such as added illumination, smoke evacuation, saline delivery, an extendable or rotatable shaft, a bendable tip, or other ancillary features.

In the case of an electrosurgical device that also provides added illumination (viz. light directed at the surgical field), the light desirably is emitted near the distal end of the device, where any added bulk may also directly impede the surgeon's view. Device designers have consequently sought to minimize the distal profile of such devices, and to make the associated components as small, thin and few in number as possible. At the same time, device designers have sought to meet an expressed desire of surgeons for as much light as possible provided at the point of dissection.

Figure 2:
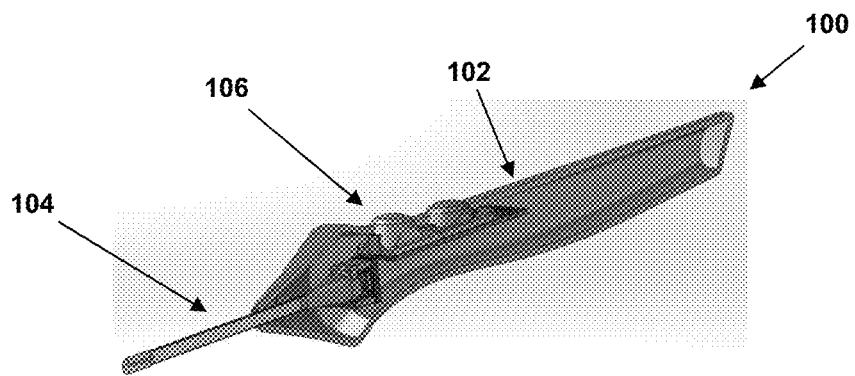
FIG. 2 depicts an internal view of the electrosurgical device of FIG. 1.

Referring to FIGS. 1 and 2, an embodiment of an electrosurgical device 100 is depicted. Generally, electrosurgical device 100 comprises a handpiece 102, blade assembly 104 and switch assembly 106. Handpiece 102 provides both a comfortable handle for a user to grip during use of device 100 and a housing for blade assembly 104 and switch assembly 106. In some embodiments, handpiece 102 can be coupled to an external power source via an electrical cable (not shown in FIG. 1 or 2) or house a power source, such as one or more batteries (also not shown in FIG. 1 or 2).

Other general features of electrosurgical device 100 are described in U.S. Pat. No. 7,736,361, US 2017/0172646 and US 2016/0120592, which are incorporated herein by reference to the extent each is consistent with the instant disclosure.

Figure 3:
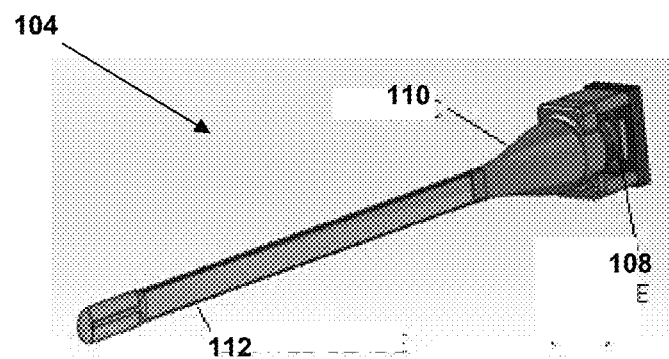
FIG. 3 depicts a blade assembly of the electrosurgical device of FIG. 1.
Figure 4:
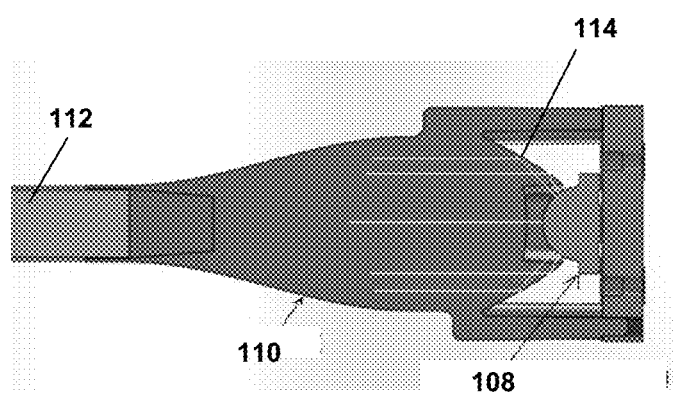
FIG. 4 depicts an optic and LED of the blade assembly of FIG. 3.

Referring to FIGS. 3 and 4, blade assembly 104 comprises a light source 108, an optic 110 and a blade 112. Light source 108 can comprise a light emitting diode (LED) light source, incandescent light source, or other suitable type of light source in various embodiments. Light source 108 can comprise a single light element (e.g., a single LED) or a plurality of light elements (e.g., multiple LEDs). Operation of light source 108 can be controlled by switch assembly 106 such that light source 108 can be selectively turned on or off. In some embodiments, additional control of light source 108 or a characteristic thereof (e.g., direction, brightness, size) can be controlled by switch assembly 106 or another component of device 100.

Light source 108 is arranged proximate optic 110. In one embodiment, optic 110 is a clear optic component configured to direct light from light source 108 (at a proximal end of optic 110) to blade 112 (at a distal end of optic 110). In some embodiments, optic 110 can comprise a lens 114, such as a collimator total internal reflection (TIR) lens, at the proximal end to direct light in a more linear manner distally. This is depicted in FIG. 4, with the horizontal lines in optic 110 representing light from light source 108 being directed by lens 114 from the larger proximal end of optic 110 to the smaller distal end of optic 110, and then to blade 112.

Optic 110 can comprise a clear molded material, such as resin, plastic, polycarbonate, acrylic, glass or another suitable material. In one embodiment, optic 110 and lens 114 comprise a unitary molded component, while in other embodiments optic 110 and lens 114 can comprise separate, distinct components mounted adjacent to and optically coupled with one another. As depicted in FIG. 4, optic 110 has a generally circular cross-section, with a portion that widens from lens 114 and then tapers towards blade 114, where the cross-section becomes rectangular. In various embodiments, optic 110 can be sized to fit a corresponding LED or other lighting component of light source 108 and have side walls congruent with a TIR surface or lens while also being configured to mate with blade 112.

Figure 5:
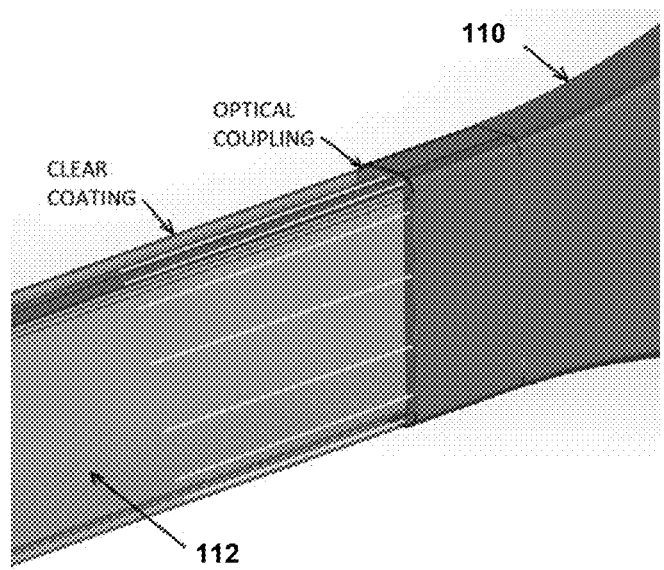
FIG. 5 depicts a detail view of an optical coupling of the blade assembly of FIG. 3.

Referring also to FIG. 5, the distal end of optic 110 is optically coupled to a proximal end of blade 112. Blade 112 also can be referred to as an electrode and, in use, can be used to cut or coagulate soft tissue of a patient. In various embodiments, blade 112 can telescope and be locked at a desired length, have a bendable shaft, include suction, and comprise many different tip configurations and designs to accommodate a variety of medical procedures. The optical and illumination features discussed herein can be compatible with some or all of these variations of blade 112, providing customizability and flexibility desired by surgical users.

Figure 6:
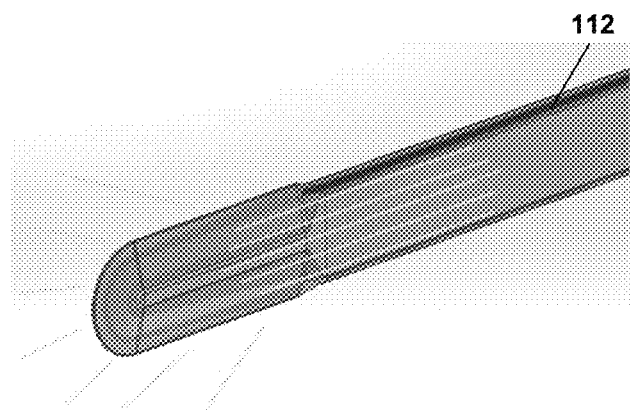
FIG. 6 depicts a detail view of a distal tip of a blade of the blade assembly of FIG. 3.

Blade 112 comprises a metal or metal alloy, such as steel, in embodiments and is coated with a dielectric material (or insulator), which focuses RF energy applied to blade 112 to achieve incisions with minimal thermal damage to the tissue. In one example, the dielectric material comprises glass. Other example dielectric materials include porcelain or ceramic, mica, plastics, and the oxides of some metals. In embodiments in which blade 112 is coated with glass, the glass can be clear and used as a conduit for light into the surgical site. Thus, the optical coupling of optic 110 with blade 112 enables light from light source 108 to be guided and directed to a distal end of blade 112 via optic 110 and the dielectric coating on blade 112. From the distal end of blade 112, the light is directed out of the dielectric coating to illuminate the area around the distal tip of blade 112, such as a surgical site. This is depicted in FIG. 6.

Figure 7:
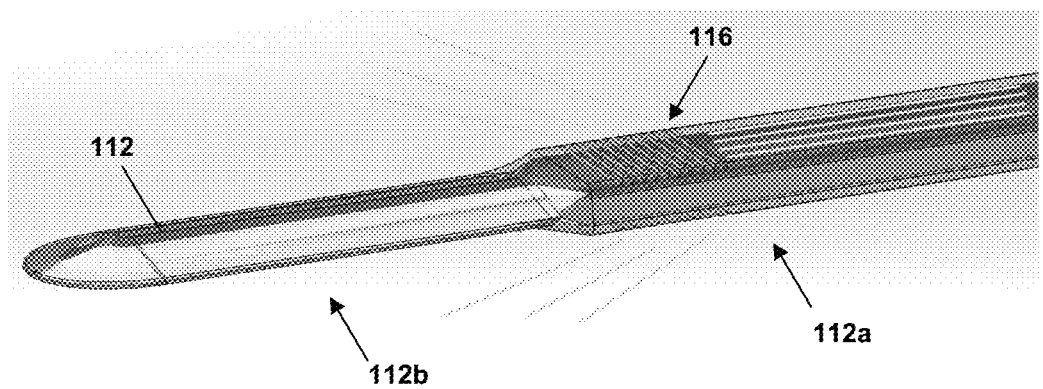
FIG. 7 depicts a blade of an electrosurgical device according to an embodiment.

Referring to FIG. 7, the dielectric coating and blade 112 can comprise at least one light-guiding feature, which can be customized to influence or direct the light in particular directions. In this embodiment, a set of grooves 116 is formed in or on blade 112 and causes light to be directed out of the dielectric coating applied on blade 112 in a particular way, direction or pattern. The location, size, number, and pattern of grooves 116 can vary in other embodiments in order to provide particular light effects. For example, grooves 116 can be linear, arcuate, zig-zag, random or comprise one or more geometric shapes, such as a circle, square, triangle, polygon or other shape. In still other embodiments, features other than grooves, such as raised portions or patterns, additional coatings or layers, or embedded elements, can be incorporated in order to provide desired light effects. Grooves 116 also can comprise combinations of these features or shapes and can be located on a proximal portion 112a or a distal portion 112b (or both) of blade 112. The thickness of the dielectric coating, with or without grooves 116 or other features discussed herein below, can range from about 1 micron to about 100 microns, such as from about 1 micron to about 10 microns, from about 1 micron to about 50 microns, from about 10 microns to about 100 microns, from about 10 microns to about 90 microns, from about 50 microns to about 100 microns, from about 20 microns to about 80 microns, from about 30 microns to about 70 microns, from about 40 microns to about 60 microns, from about 60 microns to about 90 microns, or some other range within the range bounded by 1 micron and 100 microns. In still other embodiments, the thickness of the dielectric coating can be greater than 100 microns.

Figure 8:
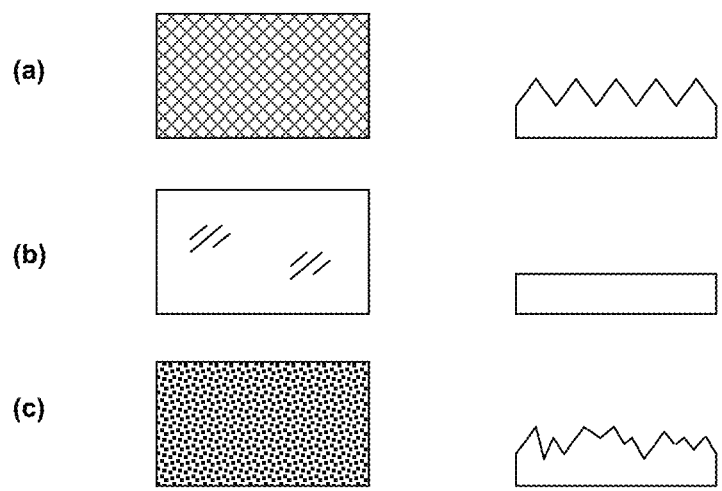
FIG. 8 depicts blade coating patterns.

Referring also to FIG. 8 (which is not necessarily drawn to scale), several examples of patterns or features other than grooves 116 are depicted. These patterns or features, like those discussed with respect to FIG. 7, can be three-dimensional. At (a) in FIG. 8, a prism pattern is shown. While the prism pattern depicted at (a) is regular, in other embodiments it can be irregular, with prisms of varying sizes or heights or interspersed with other shapes or features, such as flat areas or grooves. Systemized patterns other than prisms can be used in other embodiments. At (b), a smooth, highly polished optical quality surface example is shown. In one embodiment, a portion or the entire surface of (b) can be reflective (i.e., mirrored). At (c), a random pattern, such as might result from a surface being grit-blasted or bead-blasted, is shown. One or more of these patterns or features or those discussed with respect to FIG. 7 can be incorporated in the dielectric layer or on one or more areas of blade 112, on the entirety of the dielectric layer or blade 112, or combined with other features or elements on some or all of blade 112 in various embodiments in order to provide a desired light effect.

Figure 9:
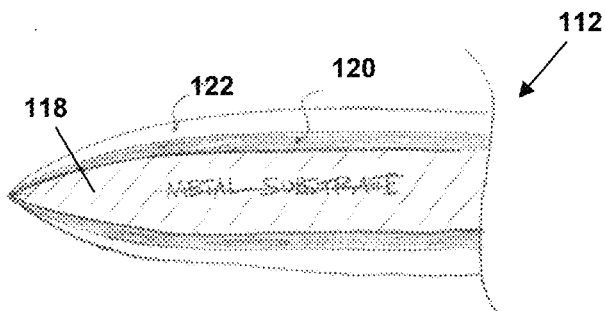
FIG. 9 depicts a cross-sectional view of a portion of a blade of an electrosurgical device according to an embodiment.

In still other embodiments, and referring to FIG. 9, blade 112 or the dielectric layer can comprise or have a multi-layered configuration to tailor the optical properties to achieve a desired outcome. In one example, the dielectric layer on blade 112 can be stratified, comprising a first or base layer 120 and a second or top layer 122 on a substrate 118 of blade 112. In other embodiments, either substrate 118 or the dielectric layer thereon can comprise more or fewer layers. In still other embodiments, layers of other materials in addition to the dielectric layer also can be incorporated.

In an embodiment with multiple layers such as first layer 120 and second layer 122, the optical properties of the respective layers can vary from one another. For example, each layer 120, 122 can have optical properties that are altered by adding pigments or composites, or by varying the degree of crystallinity of the material of the layer 120, 122.

Example pigments include P4055 blue, manufactured by Prince Minerals, Inc.; P4020 green, manufactured by Prince Minerals, Inc.; and F6333 black, manufactured by Ferro Corporation. Other pigments in these or other colors, or combinations of these or other colors, also can be used.

Example composites include adding a ceramic material, such as one or more of $Al_2O_3$, $ZrO_2$, or $TiO_2$, to first layer 120 or second layer 122 to absorb light and show a white color.

Modifying crystallinity of first layer 120 or second layer 122 can change the way light is reflected off the surface of blade 112. Increasing crystallinity will increase the diffused reflection, creating a matte finish. Reducing crystallinity will increase the specular reflection, like a mirror, or glossy. In one embodiment, an insulator crystallizing glass at 1.1 vol % crystallinity has a glossness of 108 gloss units (GU). In another embodiment, at 65 vol % crystallinity the glossness is 7.4 GU.

In a particular example related to FIG. 9, first layer 120 can be applied directly to substrate 118 of blade 112 and have absorptive properties, while second layer 122 can be applied onto first layer 120 and have highly transmittive properties. Other combinations of layers with these or other optical properties can be selected and used in other embodiments in order to achieve a desired light-effective result. Each layer need not be applied over an entirety of substrate 118 of blade 112, such that different portions of blade 112 can comprise more or fewer layers with the same or different optical properties. Additionally, one or more layers of a multi-layered dielectric also can comprise one or more of the features discussed with respect to FIGS. 7 and 8 or other features discussed herein.

Figure 10:
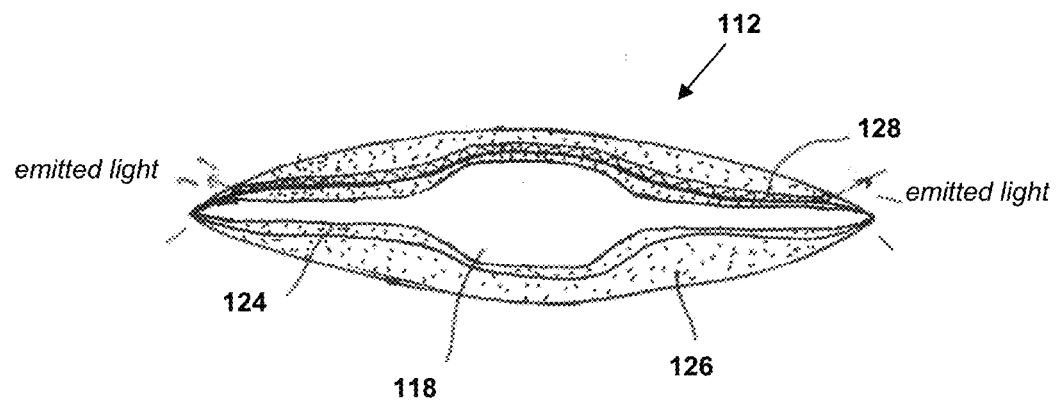
FIG. 10 depicts another cross-sectional view of a portion of a blade of an electrosurgical device according to an embodiment.

Referring to FIG. 10, which depicts a cross-section of blade 112, in some embodiments blade 112 can comprise additional light-guiding or light-influencing elements in order to achieve desired light-guiding effects. In the embodiment depicted in FIG. 10, and similar to the embodiment of FIG. 9, substrate 118 of blade 112 comprises a multi-layered coating. A base coating 124 is applied onto substrate 118 to provide adhesion and insulation and fulfill mechanical, thermal and electrical requirements of blade 112, considering that a primary purpose of blade 112, as part of device 100, is electrosurgery. A top coating 126 is applied over base coating 124 and, in one embodiment, comprises an optical fiber 128 or other optical element embedded therein. Top coating 126 can be optimized for optical properties (while still meeting dielectric strength and other requirements of electrosurgical device 100) and can comprise glass or another suitable material, including materials discussed elsewhere herein. Base coating 124 can comprise the same or a different material than top coating 126.

The process of applying top coating 126 over base coating 124 on blade 112 can comprise firing to fuse optical fiber 128, which also can comprise glass or pure silica fiber, in top coating 126 or between top coating 126 and base coating 124. Optical fiber 128 and top coating 126 have softening temperature requirements such that the temperature should be close to or higher than the firing temperature of base coating 124 so that the embedded optical fiber 128 is not deformed, and is able to trap light within optical fiber 128. In one embodiment, the firing temperature of base coating 124 is about 800 C, and the softening temperature of optical fiber 128 and top coating 126 is close to or higher than 800 C.

The difference in refractive indices between top coating 126 and optical fiber 128 will result in light being confined to optical fiber 128. In other embodiments, optical fiber 128 can comprise a glass core and glass cladding and therefore itself have a difference in refractive indices between these layers.

Figure 11:
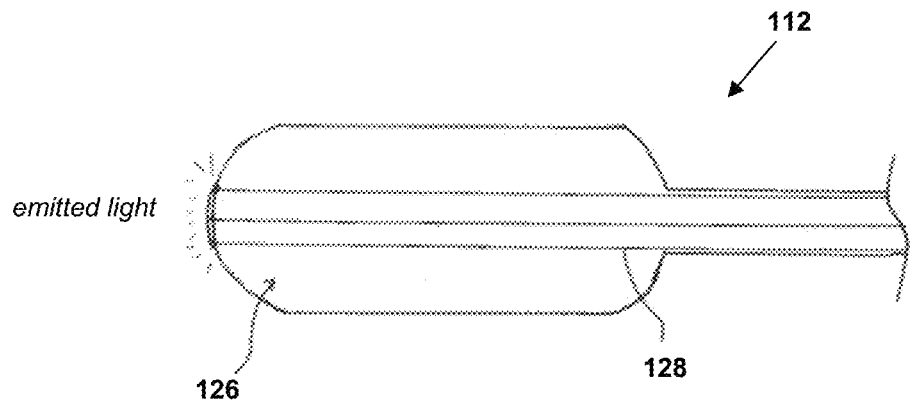
FIG. 11 depicts a detail view of a distal tip of a blade of an electrosurgical device according to an embodiment.

The material(s) of top coating 126 can be selected to meet desired optical requirements or effects. For example, top coating 126 can be colored, such as green or blue, or transparent. In one particular embodiment, top coating 126 can comprise a light absorptive material such that light is emitted only from optical fiber 128 at a distal tip of blade 112 where optical fiber 128 is exposed to air (see FIG. 11 and related discussion). In one embodiment, a light absorptive material comprises black pigment (e.g., F6333 manufactured by Ferro Corporation). An advantage of such an embodiment is that a non-transparent coating will not show the underlying light path through optical fiber 128 along blade 112, which may be preferred by users. As discussed with respect to FIGS. 7 and 8, top coating 126 also can comprise grooves 116 or other light-influencing features.

Figure 12:
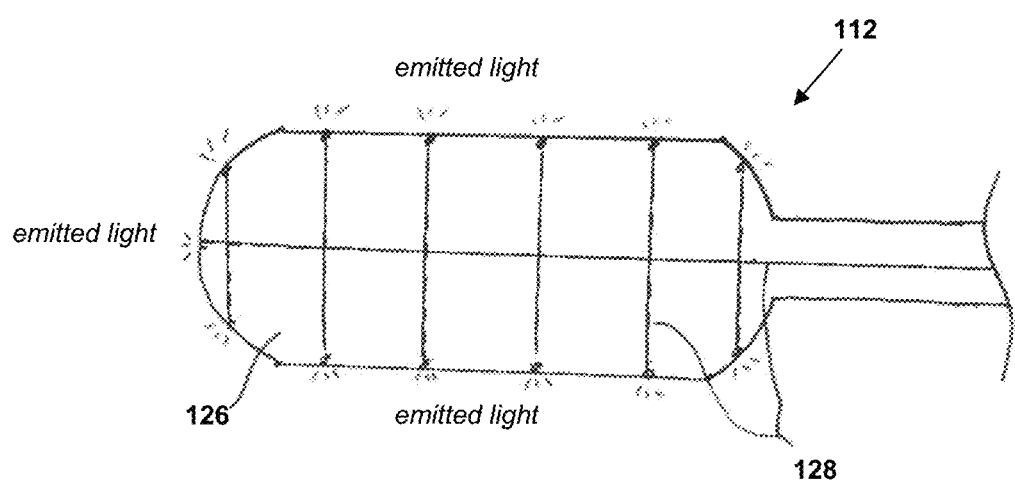
FIG. 12 depicts another detail view of a distal tip of a blade of an electrosurgical device according to an embodiment.

As depicted in FIG. 10, optical fiber 128 is embedded on only one side of blade 112. In other embodiments optical fiber 128 can be embedded on both sides of blade 112 or have some other configuration (e.g., embedded only along a central portion of blade 112, or embedded in an array on one or both sides of blade 112). For example, and referring to FIG. 11, a plurality of optical fibers 128 can be embedded in coating 126 in an arrangement that results in light emitted at the distal tip of blade 112. In such an embodiment, base coating 124 can comprise glass, and top coating 126 can comprise a colored dielectric glass. A similar embodiment with an alternate arrangement of optical fibers 128 is depicted in FIG. 12. In FIG. 12, optical fibers 128 are arranged in a grid-like pattern such that light is emitted around an entire cutting edge of the distal tip of blade 112. Such a configuration can give a surgeon user a more precise view of a cutting location regardless of the orientation of blade 112 during use. Various other arrangements of optical fibers 128 can be implemented in other embodiments in order to provide a desired lighting effect, as appreciated by those of skill in the art.

Figure 13:
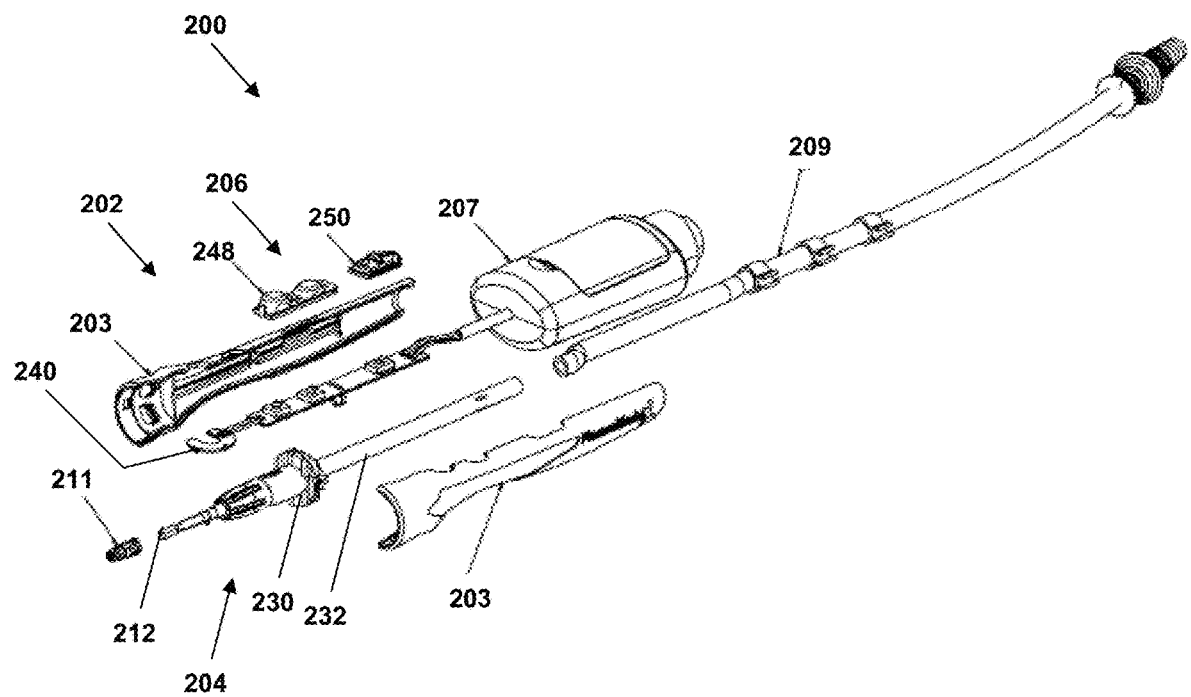
FIG. 13 depicts an exploded view an electrosurgical device according to an embodiment.

Another embodiment of an illuminated electrosurgical device 200 is depicted in FIG. 13. Device 200 comprises a handpiece 202 (like numbers are used herein throughout, incremented by 100, unless otherwise discussed), blade assembly 204, switch assembly 206, cable assembly 207, suction tubing assembly 209, and finger grip 211. Handpiece 202 comprises a housing 203, which houses blade assembly 204, switch assembly 206, and other components of device 200. Device 200 can comprise additional components, some of which are depicted but not particularly discussed.

Figure 14:
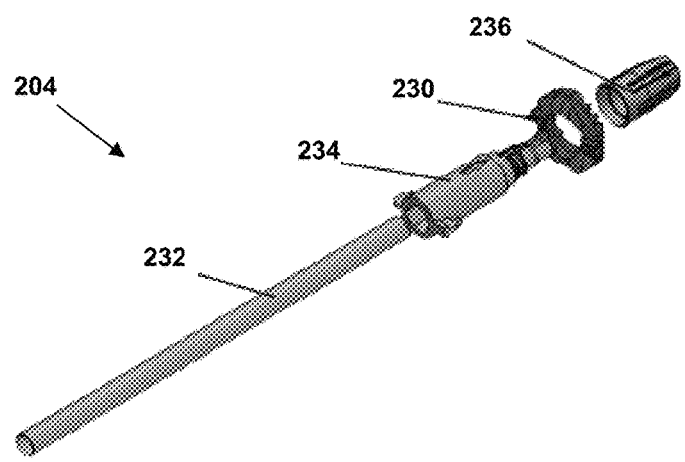
FIG. 14 depicts an exploded view of a blade assembly of the electrosurgical device of FIG. 13.

With respect to illumination in particular, and referring also to FIG. 14, blade assembly 204 comprises a ring lens 230 arranged around a central shaft 232 of blade assembly 204, coupled to a hub 234. Ring lens 230 is arranged at a distal end of handpiece 202, centered on central shaft 232. Blade assembly 204 also comprises a lock nose cone 236 that couples to hub 234.

Figure 15:
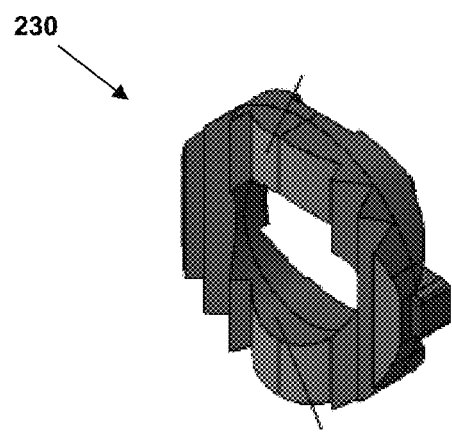
FIG. 15 depicts a first side of a Fresnel lens according to an embodiment.
Figure 16:
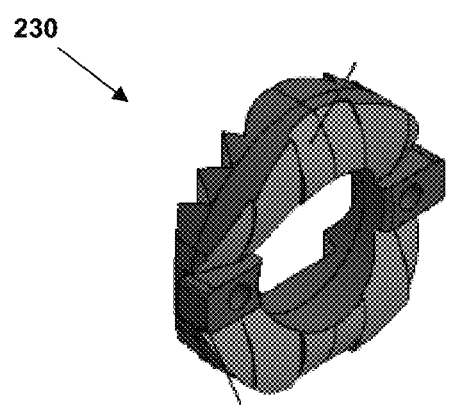
FIG. 16 depicts a second side of the Fresnel lens of FIG. 15.
Figure 17:
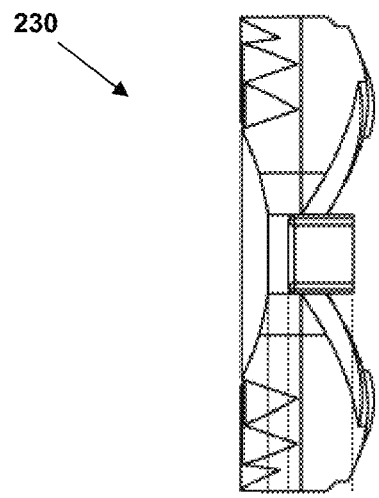
FIG. 17 depicts a side view of the Fresnel lens of FIG. 15.
Figure 18:
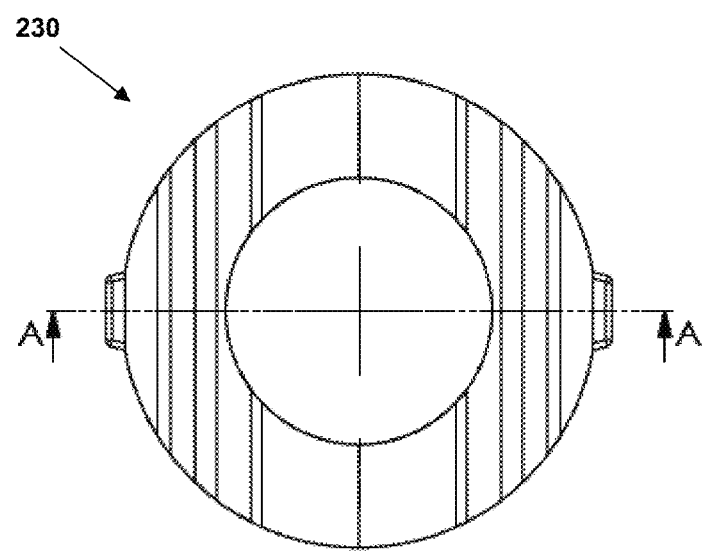
FIG. 18 depicts another view of the Fresnel lens of FIG. 15.
Figure 19:
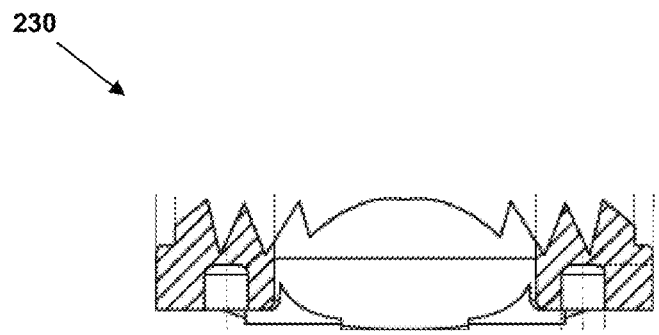
FIG. 19 depicts a cross-sectional view of the Fresnel lens of FIG. 15, taken along line A-A in FIG. 18.

Ring lens 230 is depicted in greater detail in FIGS. 15-19. In the depicted embodiment, ring lens 230 comprises a Fresnel lens. A typical Fresnel lens comprises a series of facets or prisms that focus or magnify light. These facets can be seen in FIGS. 15 and 16. FIG. 15 depicts one configuration of facets on a front side of ring lens 230, while FIG. 16 depicts one configuration of facets on a back side of ring lens 230. Ring lens 230 can comprise acrylic, polycarbonate, or some other transparent material. Surfaces of ring lens 230, such as the major surfaces visible in FIGS. 15 and 16, can be textured, such as according to texture grade MT-11006 in one example. In some embodiments, ring lens 230 can comprise total internal reflection (TIR) surfaces, which can maximize the light that is first reflected within and then exited from ring lens 230. Ring lens 230 also can be considered to be a light pipe.

In device 200, ring lens 230 can focus light from a light source (discussed herein below) and direct the light around a tip of blade 212 of blade assembly 204. The dimensions of ring lens 230 and configuration of the facets thereof can be optimized to provide a particular illumination effect. In one embodiment, ring lens 230 has a diameter of approximately 0.78 inches and is about 0.2 inches thick. Such a ring lens 230 can provide an approximately 2-inch circle of light around a distal tip of blade 212 in use. The diameter can vary from about 0.5 inches to about 1.0 inches, and the thickness can range from about 0.1 inches to about 0.25 inches. Adjusting the size or dimensions of features of ring lens 230 can provide other illumination effects, as may be desired in particular applications or uses. Dimensions can be selected such that an outer diameter of ring lens 230 does not block a user's view while at the same time being large enough to provide a light angle that minimizes shadow at the tip of blade 112.

Figure 20:
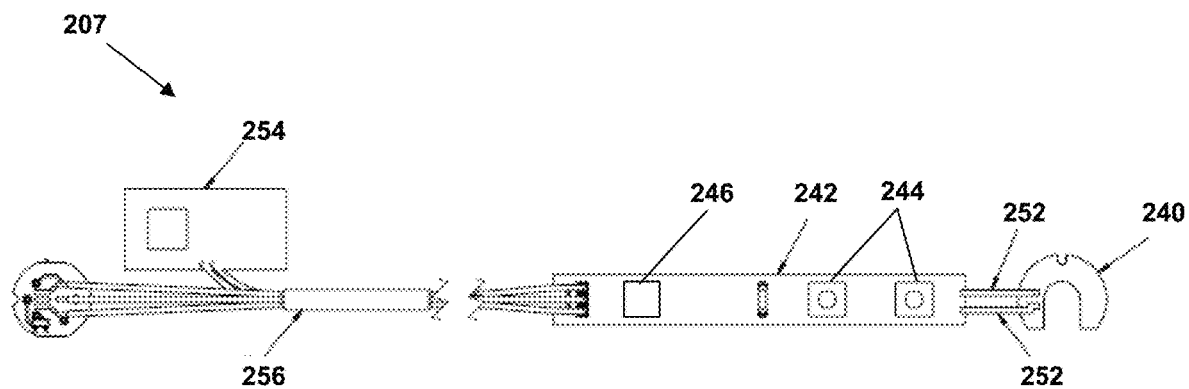
FIG. 20 depicts a cable assembly of the electrosurgical device of FIG. 13.

Light can be provided by one or more light emitting diodes (LEDs) arranged on an LED printed circuit board (PCB) 240 of cable assembly 207, which is depicted in FIGS. 13 and 20. The LEDs can comprise chip on board (COB) LEDs, which can comprise a plurality of LED chips. COB LEDs can take up less space and be bonded directly to a substrate, which can be LED PCB 240. LED PCB 240 can comprise a partial or full ring configuration, which can be sized and arranged such that COB LEDs mounted thereon provide light directly to ring lens 230.

LED PCB 240 is coupled to a light handle PCB 242, which includes contacts 244 and 246 for switch assembly 206. In particular, contacts 244 electrically couple with a main button pad 248 of switch assembly 206, and contact 246 electrically couples with a light switch 250 of switch assembly 206. In one embodiment, main button pad 248 comprises one or more PANASONIC® EVQQ2 switches by which device 200 can be turned on and off and otherwise controlled, and light switch 250 comprises a slider switch by which illumination of device 200 can be turned on and off. Other types of switches can be used in other embodiments. In another embodiment, illumination can be automatically turned on or off when device 200 is turned on or off, respectively. In still another embodiment, device 200 must first be turned on via main button pad 248 before illumination can be turned on via light switch 250. Wires 252 electrically couple LEDs on LED PCB 240 to light handle PCB 242 and light switch 250.

Figure 21:
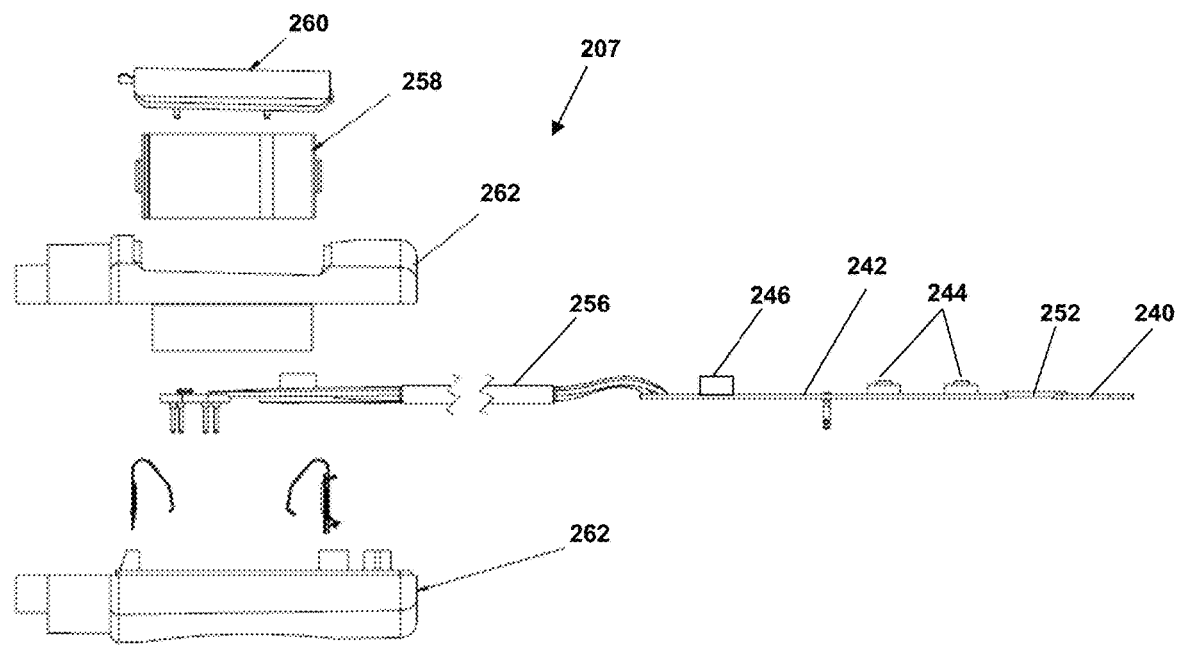
FIG. 21 depicts an exploded view of the cable assembly of the electrosurgical device of FIG. 13.

Referring also to FIG. 21, LEDs on LED PCB 240 or device 200 overall can be powered by an external power source or an internal battery 258. An internal battery can be disposable and replaceable, or rechargeable. In one embodiment, at least one lithium CR-123 battery is housed in cable assembly 207 and coupled to LED PCB 240 via light handle PCB 242, which is in turn coupled to battery control circuitry on a battery control PCB 254 by a cable 256. Battery 258 can be accessed via a battery door 260 in a connector 262 of cable assembly 207. Batteries other than lithium or CR-123 can be used in other embodiments.

Figure 22:
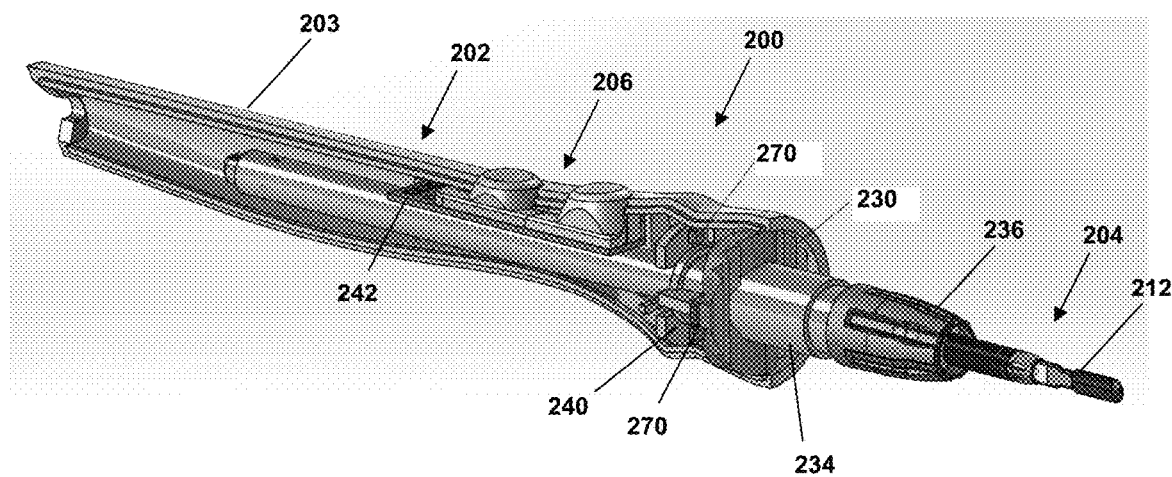
FIG. 22 depicts an internal view of an electrosurgical device according to an embodiment.
Figure 23:
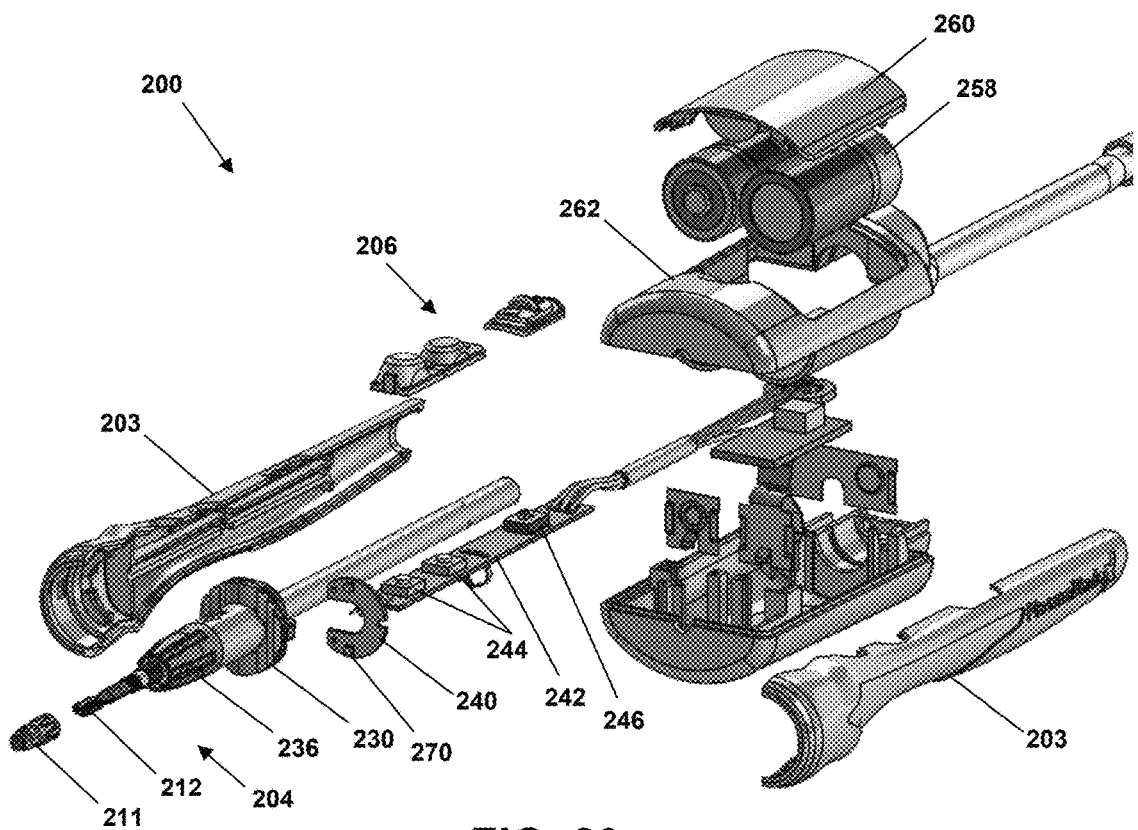
FIG. 23 depicts an exploded view of the electrosurgical device of FIG. 22.

As previously mentioned, LED PCB 240 can comprise a partial or full ring configuration that is sized and arranged such that COB LEDs mounted thereon provide light directly to ring lens 230. This can be seen in FIGS. 22-26. The embodiment of FIGS. 22-24 comprises two LEDs 270, while the embodiment of FIG. 25 comprises four LEDs 270. FIG. 26 is an enclosed housing view of device 200 and can comprise two, four or some other number of LEDs 270.

Figure 24:
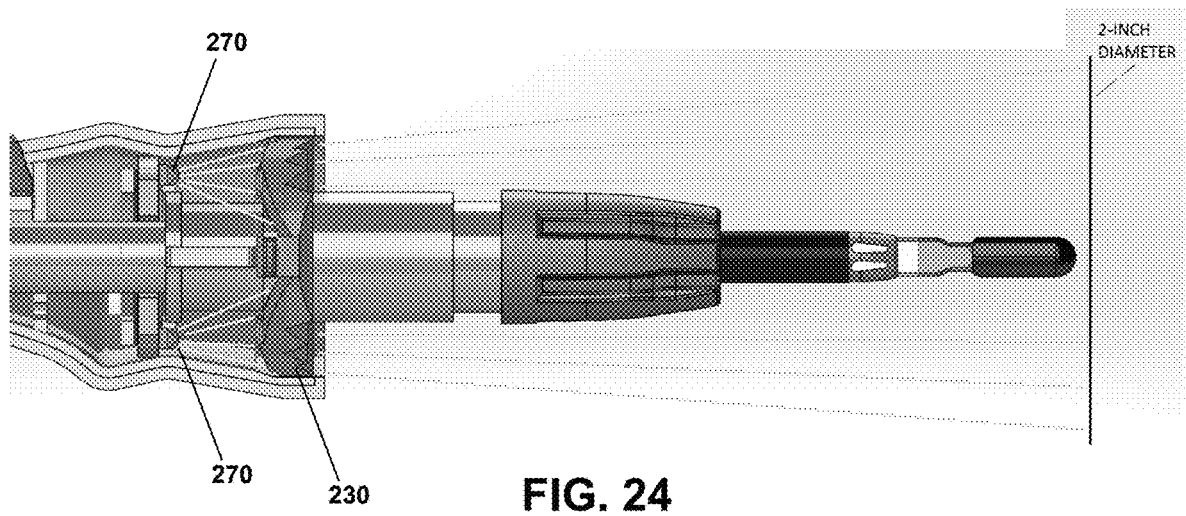
FIG. 24 depicts another view of the electrosurgical device of FIG. 22.

Referring in particular to FIG. 24, in operation light from LEDs 270 is directed into ring lens 230, which concentrates the light into a circle around a distal tip of blade 212. In the embodiment of FIG. 24, light is concentrated into a circle with a diameter of about 2 inches, though in other embodiments this diameter can be made larger or smaller, or comprise a different shape, by adjusting properties of ring lens 230.

Figure 25:
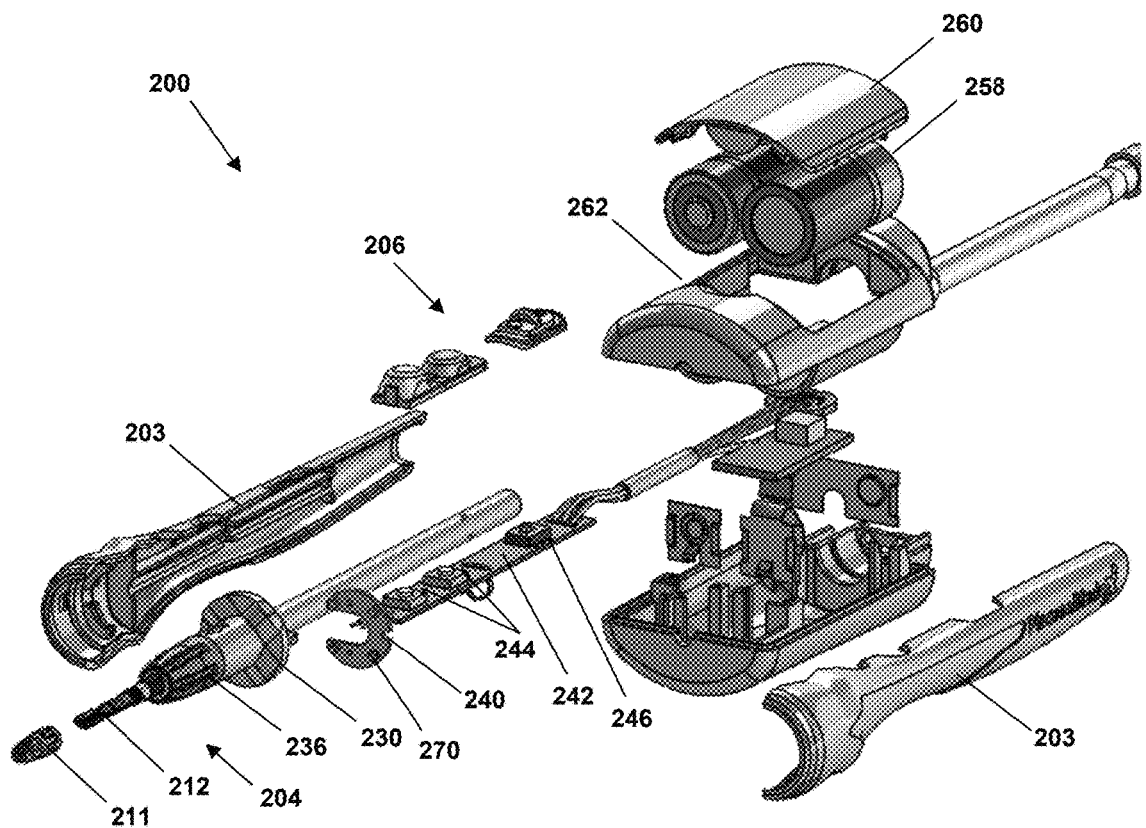
FIG. 25 depicts an exploded view an electrosurgical device according to an embodiment.
Figure 26:
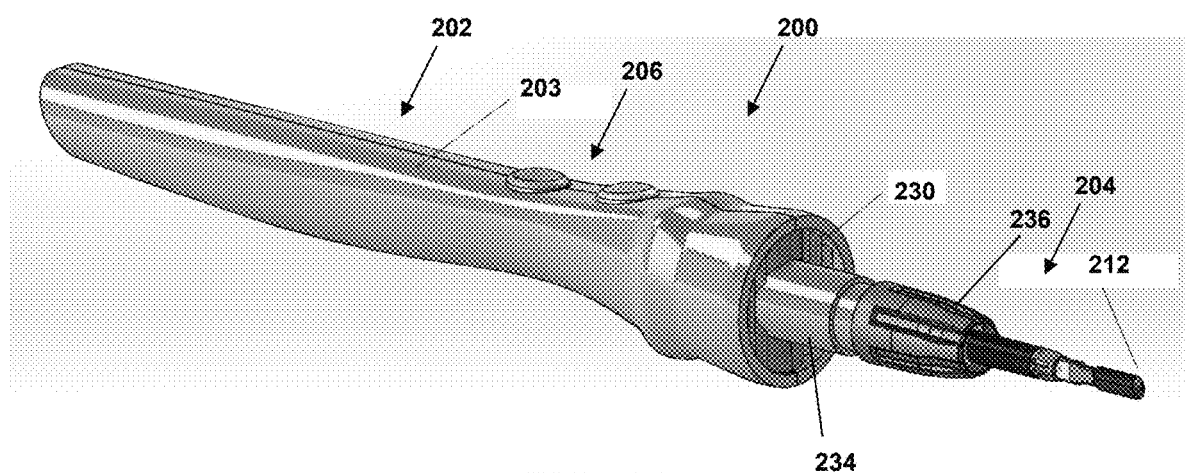
FIG. 26 depicts another view of the electrosurgical device of FIG. 22.

The same principles apply to the embodiment of FIG. 25, which comprises four LEDs 270. As can be seen in FIG. 25, each of the four LEDs 270 can be evenly spaced apart (e.g., by about 90 degrees) from one another along a circumference on LED PCB 240. Other embodiments can comprise more or fewer LEDs 270, which can be similarly arranged with even spacings along a circumference on LED PCB 240 or in some other arrangement chosen, for example, to provide a particular illumination effect.

Figure 27:
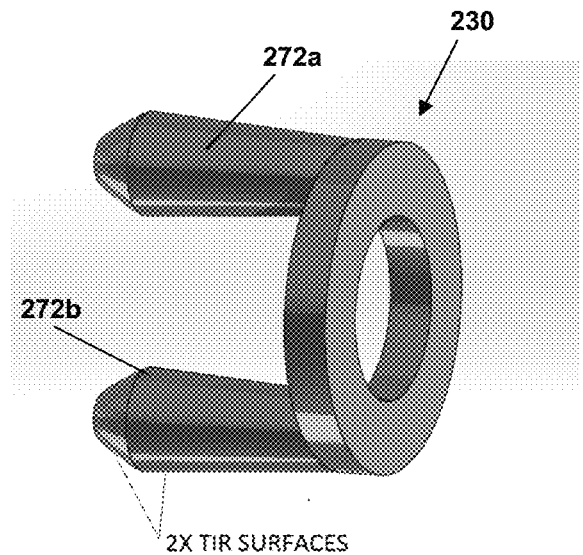
FIG. 27 depicts a lens for an electrosurgical device according to an embodiment.
Figure 28:
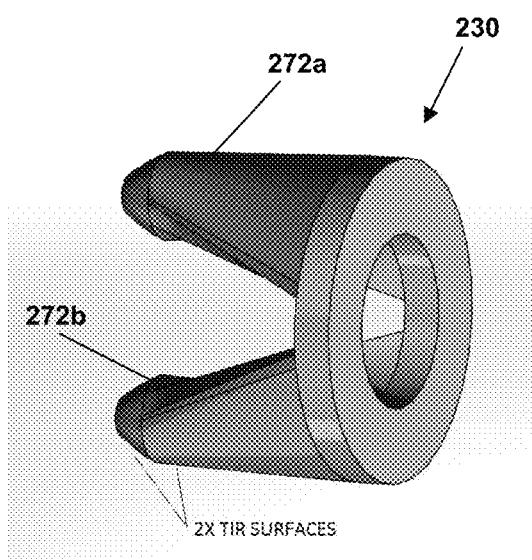
FIG. 28 depicts another lens for an electrosurgical device according to an embodiment.

Lens 230 also can be differently configured in other embodiments to provide a particular light effect in cooperation with one or more LEDs 270. For example, in FIG. 27 lens 230 can comprise two legs 272a and 272b, each leg 272a, 272b configured such that a proximal end is arranged relative to a respective LED 270 to receive light therefrom. The proximal end of each leg 272a, 272b can comprise a collimator in the form of two TIR surfaces to reflect light internally to lens 230, thereby concentrating and controlling the light to provide illumination in a desired pattern around the distal tip of blade 212. In embodiments in which device 200 comprises more or fewer LEDs, lens 230 can correspondingly comprise more or fewer legs 272a, 272b. Still other configurations of lens 230 are possible, as appreciated by those of skill in the art. For example, different shapes of lens 230 or legs 272a, 272b can be implemented, as can different configurations of TIR surfaces on legs 272a, 272b or lens 230.

In yet another embodiment, device 200 can comprise additional components or features to provide increased or desired illumination effects. For example, device 200 can comprise additional collimating features or lenses. In another example, LEDs 270 can comprise or be configured for particular light effects, such as comprising a collimator or other feature on the significant surface thereof to direct light. In yet another example, LEDs 270 can be arranged on LED PCB 240 or otherwise positioned in light-effective ways, such as at an angle, including orthogonally. In still another embodiment, a color or colors of LEDs 270 can be selected to provide brighter or more desired light, such as white light. LEDs 270 also may be arranged to be user-manipulated in some embodiments, such as to be brightened or dimmed (intensity variation) or mechanically moveable, such as closer or further from the distal tip of blade 212 or relative to lens 230 in order to tune a size or other characteristic of the light directed towards the distal tip of blade 212.

Several advantages are provided by embodiments discussed herein. These include compatibility of ring lens 230 of the illumination system with other features of electrosurgical device, such as extendability and rotation, as well as a bendable tip, of blade assembly 204, and smoke evacuation. This is possible because of the ring configuration of ring lens 230, which enables other components to pass through.

Features and components of different embodiments discussed herein can be combined in other embodiments. For example, blade coatings and optical fibers discussed with respect to device 100 can be incorporated into embodiments of device 200, and vice-versa. In this was particular illumination effects can be designed and achieved in order to meet particular desires or needs in the industry.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An electrosurgical device comprising:
an electrosurgical blade having a proximal end and a distal end and comprising a dielectric coating, at least one of the electrosurgical blade or the dielectric coating including at least one light-guiding element comprising at least one groove formed on the electrosurgical blade or the dielectric coating at a location proximal of the distal end of the electrosurgical blade, the at least one groove oriented to direct light through the dielectric coating towards the distal end of the electrosurgical blade, wherein the dielectric coating includes the at least one light-guiding element;

an optic having a proximal end and a distal end, the distal end of the optic optically coupled to the proximal end of the electrosurgical blade; and a light source arranged at the proximal end of the optic and configured to provide light through the optic and into the dielectric coating, the dielectric coating and the at least one light-guiding element configured to guide light from the optic through the dielectric coating, and out of the dielectric coating near the distal end of the electrosurgical blade to illuminate an area around the distal end of the electrosurgical blade.

2. The electrosurgical device of claim 1, wherein the light sources comprises at least one light-emitting diode (LED).

3. The electrosurgical device of claim 1, wherein the optic comprises a lens at the proximal end of the optic.

4. The electrosurgical device of claim 3, wherein the lens is a collimator total internal reflection (TIR) lens.

5. The electrosurgical device of claim 1, wherein the dielectric coating comprises glass.

6. The electrosurgical device of claim 1, wherein the illuminated area around the distal end of the electrosurgical blade has a diameter of about two inches.

7. The electrosurgical device of claim 1, wherein the at least one groove is formed on the electrosurgical blade.

8. The electrosurgical device of claim 1, wherein the at least one groove is formed on the dielectric coating.

9. An electrosurgical device comprising,
an electrosurgical blade having a proximal end and a distal end and comprising a dielectric coating, at least one of the electrosurgical blade or the dielectric coating including at least one light-guiding element comprising at least one pattern of texture formed on the electrosurgical blade or the dielectric coating at a location proximal of the distal end of the electrosurgical blade, the at least one pattern of texture oriented to direct light through the dielectric coating towards the distal end of the electrosurgical blade, wherein the dielectric coating includes the at least one light-guiding element;

an optic having a proximal end and a distal end, the distal end of the optic optically coupled to the proximal end of the electrosurgical blade; and a light source arranged at the proximal end of the optic and configured to provide light through the optic and into the dielectric coating, the dielectric coating and the at least one light-guiding element configured to guide light from the optic through the dielectric coating, and out of the dielectric coating near the distal end of the electrosurgical blade to illuminate an area around the distal end of the electrosurgical blade.

10. The electrosurgical device of claim 9, wherein the dielectric coating is a multi-layered dielectric coating comprising a base layer and a top layer.

11. The electrosurgical device of claim 10, wherein at least one of a pigment, a composite content or a degree of crystallinity varies from the base layer to the top layer.

12. The electrosurgical device of claim 10, wherein at least one optical element is embedded in the multi-layered dielectric coating.

13. The electrosurgical device of claim 12, wherein the at least one optical element is an optical fiber.

14. The electrosurgical device of claim 12, wherein an array of optical fibers are embedded in the multi-layered dielectric coating.

15. The electrosurgical device of claim 9, wherein the pattern of texture comprises raised features.

16. The electrosurgical device of claim 9, wherein the pattern of texture comprises prisms.

17. The electrosurgical device of claim 9, wherein the pattern of texture is random.

18. The electrosurgical device of claim 9, wherein the pattern of texture is formed on the electrosurgical blade.

19. The electrosurgical device of claim 9, wherein the pattern of texture is formed on the dielectric coating.

20. A method comprising:
coating an electrosurgical blade having a proximal end and a distal end with a dielectric layer;

forming at least one light-guiding element on at least one of the electrosurgical blade or the dielectric layer at a location proximal of the distal end of the electrosurgical blade including forming at least one groove on the electrosurgical blade or the dielectric coating as the at least one light-guiding element, the at least one groove oriented to direct light through the dielectric coating towards the distal end of the electrosurgical blade;

optically coupling a distal end of an optic to the proximal end of the electrosurgical blade; and arranging a light source at a proximal end of the optic to provide light through the optic and into the dielectric coating, the dielectric coating and the at least one light-guiding element configured to guide light from the optic through the dielectric coating, and out of the dielectric coating near the distal end of the electrosurgical blade to illuminate an area around the distal end of the electrosurgical blade.

21. The method of claim 20, further comprising forming the optic to include a lens at the proximal end of the optic.

22. The method of claim 21, wherein arranging a light source further comprises arranging the light source relative to the lens of the optic such that total internal reflection (TIR) of the light occurs in the optic.

23. The method of claim 20, wherein coating an electrosurgical blade with a dielectric layer further comprises forming at least one optical fiber in the multi-layered dielectric as the at least one light-guiding element.

24. The method of claim 20, wherein forming at least one light-guiding element further comprises forming at least one pattern on the electrosurgical blade.

25. The method of claim 20, wherein forming at least one light-guiding element further comprises forming at least one pattern on the dielectric coating.

* * * * *